(12) United States Patent
Silks et al.

(10) Patent No.: US 8,497,386 B2
(45) Date of Patent: Jul. 30, 2013

(54) METHOD OF CARBON CHAIN EXTENSION USING NOVEL ALDOL REACTION

(75) Inventors: Louis A. Silks, Los Alamos, NM (US); John C. Gordon, Los Alamos, NM (US); Ruilan Wu, Los Alamos, NM (US); Susan Kloek Hanson, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/557,338

(22) Filed: Jul. 25, 2012

(65) Prior Publication Data
US 2012/0289720 A1   Nov. 15, 2012

Related U.S. Application Data

(63) Continuation of application No. 12/542,384, filed on Aug. 17, 2009, now abandoned.

(51) Int. Cl.
*C07D 307/12* (2006.01)
*C10L 1/04* (2006.01)

(52) U.S. Cl.
USPC .............................. 549/498; 549/473; 585/14

(58) Field of Classification Search
USPC ......................................... 549/472, 498, 473
See application file for complete search history.

(56) References Cited

U.S. PATENT DOCUMENTS

| | | | |
|---|---|---|---|
| 2008/0058563 | A1 | 3/2008 | Dumesic et al. |
| 2009/0124839 | A1* | 5/2009 | Dumesic et al. ............. 585/251 |
| 2011/0040109 | A1 | 2/2011 | Silks et al. |
| 2011/0040110 | A1 | 2/2011 | Silks et al. |

OTHER PUBLICATIONS

Mascal et al. Angew. Chem. Int. Ed., vol. 47, p. 7924-7926 (2008).*
Chimni et al, Tetrahedron, vol. 61, p. 5019-5025 (2005).*
Dickerson et al, J. Am. Chem. Soc., vol. 124, p. 3220-3221 (2002).*
Binder et al., "Simple Chemical Transformation of Lignocellulosic Biomass into Furans for Fuels and Chemicals", J. Am. Chem. Soc., Jan. 2009, 131(5), 1979-1985.
Darbre et al., "Zn-Proline catalyzed direct aldol reaction in aqueous media," Chem. Commun., Mar. 31, 2003, Issue 9, 1090-1091, Abstract.
Fernandez-Lopez et al., "A Selective Direct Aldol Reaction in Aqueous Media Catalyzed by Zinc-Proline", Eur. J. Org. Chem., Dec. 2005, Issue 24, 5268-5276.
Huber et al., "Production of Liquid Alkanes by Aqueous-Phase Processing of Biomass-Derived Carbohydrates", Science, Jun. 2005, 308(5727), 1446-1450.
Notification of Transmittal of the International Search Report and Written Opinion of the International Searching Authority, or the Declaration issued on Dec. 16, 2010 for International Application PCT/US10/02216 filed on Aug. 11, 2010, 16 pages.
Notification of Transmittal of the International Search Report and Written Opinion of the International Searching Authority, or the Declaration issued on Dec. 16, 2010 for corresponding International Application PCT/US10/02218 filed on Aug. 11, 2010, 12 pages.
U.S. Appl. No. 13/556,484, filed Jul. 24, 2012, Silks.
Vishnumaya et al., "Highly Efficient Small Organic Molecules for Enantioselective Direct Aldol Reaction in Organic and Aqueous Media", J. Org. Chem., May 2009, 74(11), 4289-4297.
West et al., "Carbon-carbon bond formation for biomass-derived furfurals and ketones by aldol condensation in a biphasic system", Journal of Molecular Catalysis A: Chemical, 296(1-2), Dec. 2008, 18-27.

* cited by examiner

*Primary Examiner* — Bernard Dentz
(74) *Attorney, Agent, or Firm* — Woodcock Washburn, LLP

(57) ABSTRACT

Method of producing $C_8$-$C_{15}$ hydrocarbons. comprising providing a ketone starting material; providing an aldol starting material comprising chloromethylfurfural; mixing the ketone starting material and the aldol starting material in a reaction in the presence of a proline-containing catalyst selected from the group consisting of $Zn(Pro)_2$, $Yb(Pro)_3$, and combinations thereof, or a catalyst having one of the structures (I), (II) or (III), and in the presence of a solvent, wherein the solvent comprises water and is substantially free of organic solvents, where (I), (II) and (III) respectively are:

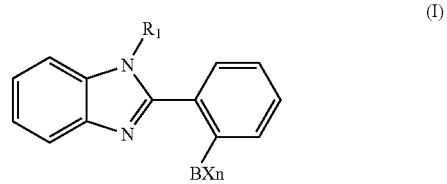

where $R_1$ is a $C_1$-$C_6$ alkyl moiety, X=(OH) and n=2.

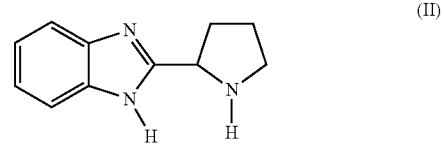

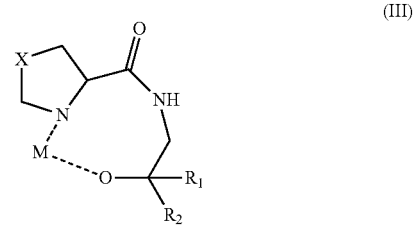

In (III), X may be $CH_2$, sulfur or selenium, M may be Zn, Mg, or a lanthanide, and $R_1$ and $R_2$ each independently may be a methyl, ethyl, phenyl moiety.

5 Claims, 4 Drawing Sheets

(a)

5-(chloromethyl)furan-2-
carbaldehyde   acetone   (E)-4-(5-(chloromethyl)furan-2-
yl)but-3-en-2-one (b)

0.5 equiv

60%

(1E,4E)-1,5-bis(5-(chloromethyl)furan-2-
yl)penta-1,4-dien-3-one

Dihydroxyacetone 4-(5-(chloromethyl)furan-2-yl)-1,3,4-trihydroxybutan-2-one

METHOD OF CARBON CHAIN EXTENSION USING NOVEL ALDOL REACTION

RELATED APPLICATIONS

This application is a continuation of U.S. application Ser. No. 12/542,384, filed Aug. 17, 2009, the entirety of which is incorporated by reference herein.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to methods of producing $C_8$-$C_{15}$ hydrocarbons from renewable feedstocks such as cellulosics, sugars and glycerin, by means of an organo-catalyzed aldol reaction.

BACKGROUND OF THE INVENTION

Development of sustainable methods of making transportation fuels and chemical feedstocks such as surfactants from renewable resources is becoming increasingly important, due to the desirability of decreasing dependence on petroleum resources. Carbohydrates obtained from biomass are renewable and readily available, and there has been much focus on producing fuel and other useful materials from biomass-derived starting materials. Other readily available starting materials include simple sugars, glycerol and the oxidation product of glycerol, dihydroxyacetone (DHA). Compounds suitable for use as chemical feedstocks generally include $C_8$-$C_{15}$ alcohols and olefins. Commercially useful surfactants may comprise from about 10 to about 22 carbon atoms. Therefore, in order to produce surfactants from biomass-derived starting materials, the carbon chain length of the starting material must be increased. One common method of achieving this is through the aldol reaction, which forms a carbon-carbon bond between an aldehyde and a ketone. Cellulosics, sugars and glycerin can readily be converted to suitable reagents for the aldol reaction. For example, cellulose and glucose can be converted to hydroxymethylfurfural (HMF). Dihydroxyacetone can be formed from glycerol.

Use of the aldol reaction with reagents derivable from cellulosics and sugars has been described previously (see, e.g., Huber et al., Science, vol. 208, Jun. 3, 2005, pp. 1446-1450). However, the reactions resulted in a range of carbon chain lengths, and thus exhibited poor selectivity. In addition, the reactions required high temperatures (approximately 100° C.), and the use of an organic solvent in addition to water. Most important, the reaction was shown to be unsuccessful with ketone reagents other than acetone. All of these factors contribute to making the process less suitable for large-scale industrial use.

The use of a zinc-proline ($Zn(Pro)_2$) catalyst has been shown to be successful in certain types of aldol reactions, and addresses some of the above drawbacks. Zinc-proline catalysts result in higher selectivity, and have been shown to work with DHA as a ketone reagent. To date, however, zinc-proline catalysts have shown only to successfully catalyze reactions between ketones and aromatic aldehydes (for example, benzaldehydes) and not between ketones and reagents derived from biomass sources, such as HMF. Although able to catalyze reactions in aqueous solvents and at lower temperatures, the reactions described to date using zinc-proline catalysts have required the addition of an organic co-solvent, such as tetrahydrofuran (THF).

There exists a need, therefore, for a method of increasing carbon chain length via the aldol reaction that utilizes reagents derived from biomass sources, is highly selective, can be performed at room temperature and does not require the use of an organic co-solvent, thus making the process more suitable for large-scale production with specificity. There exists a further need for additional catalysts that allow the aldol reaction to proceed under conditions suitable for large-scale use.

SUMMARY OF THE INVENTION

The present invention meets the aforementioned needs by providing a method of increasing carbon chain length by utilizing the aldol reaction that can be performed with either zinc-proline, ytterbium-proline, or metal chelated N-(2-hydroxy-2-methylpropyl)pyrrolidine-2-carboxamide based catalysts, and which can be performed at room temperature using only water as the solvent. The reaction utilizes DHA (and other ketones or aldehydes) as the ketone reagent and chloromethylfurfural as the aldehyde reagent, which can be obtained from biomass cellulosics. The reaction has high specificity, and results in formation of (E)-4-(5-(chloromethyl)furan-2-yl)but-3-en-2-one, (1E,4E)-1,5-bis(5-(chloromethyl)furan-2-yl)penta-1,4-dien-3-one, 3,4-dihydroxy-4-(5-(chloro-methyl)furan-2-yl)butan-2-one, (E)-5-(5-(chloromethyl)furan-2-yl)-4,5-dihydroxy-1-(5-(hydroxymethyl)furan-2-yl)pent-1-en-3-one and/or 1,3,4-trihydroxy-4-(5-(chloromethyl)furan-2-yl)butan-2-one, with a yield of 60%.

The following describe some non-limiting embodiments of the present invention.

According to one embodiment of the present invention, a method of producing $C_8$-$C_{15}$ hydrocarbons is provided, comprising providing a ketone starting material; providing an aldol starting material comprising chloromethylfurfural; and mixing the ketone starting material and the aldol starting material in a reaction in the presence of a proline-containing catalyst selected from the group consisting of $Zn(Pro)_2$, $Yb(Pro)_3$, and combinations thereof, and a solvent, wherein the solvent comprises water and is substantially free of organic solvents, to produce the $C_8$-$C_{15}$ hydrocarbons.

According to another embodiment of the present invention, a method of producing $C_8$-$C_{15}$ hydrocarbons is provided, comprising providing a ketone starting material; providing an aldol starting material; and mixing the ketone starting material and the aldol starting material in a reaction in the presence of a catalyst having the structure:

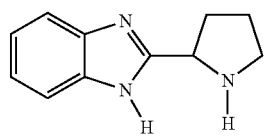 [SMILES: c1ccc2[nH]c(C3CCCN3)nc2c1]

and a solvent, wherein the solvent comprises water and is substantially free of organic solvents, to produce the $C_8$-$C_{15}$ hydrocarbons.

According to yet another embodiment of the present invention, a method of producing $C_8$-$C_{15}$ hydrocarbons is provided, comprising providing a ketone starting material; providing an aldol starting material; and mixing the ketone starting material and the aldol starting material in a reaction in the presence of a catalyst having the structure:

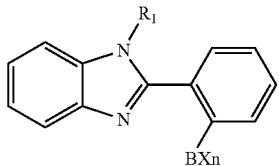

wherein R is a $C_1$-$C_6$ alkyl moiety, X=(OH) and n=2, and in the presence of a solvent, wherein the solvent comprises water and is substantially free of organic solvents, to produce the $C_8$-$C_{15}$ hydrocarbons.

According to yet another embodiment of the present invention, a method of producing $C_8$-$C_{15}$ hydrocarbons is provided, comprising providing a ketone starting material; providing an aldol starting material; and mixing the ketone starting material and the aldol starting material in a reaction in the presence of a catalyst having the structure:

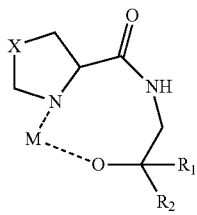

where X is $CH_2$, sulfur or selenium, M is Zn, Mg, or a lanthanide, and $R_1$ and $R_2$ each independently are a methyl, ethyl, or phenyl moiety; and in the presence of a solvent, wherein the solvent comprises water and is substantially free of organic solvents, to produce the $C_8$-$C_{15}$ hydrocarbons.

DETAILED DESCRIPTION OF THE INVENTION

Figure 1:
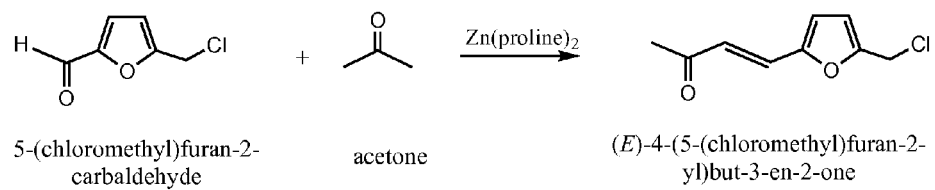
FIGS. 1(a) and (b) depict exemplary reaction schemes of the present invention, wherein chloromethylfurfural (5-(chloromethyl)furan-2-carbaldehyde) reacts with acetone (FIG. 1(a), one molar equivalent and FIG. 1(b), 0.5 molar equivalents) to form the hydrocarbon products (E)-4-(5-(chloromethyl)furan-2-yl)but-3-en-2-one and (1E,4E)-1,5-bis(5-(chloromethyl)furan-2-yl)penta-1,4-dien-3-one.
Figure 1:
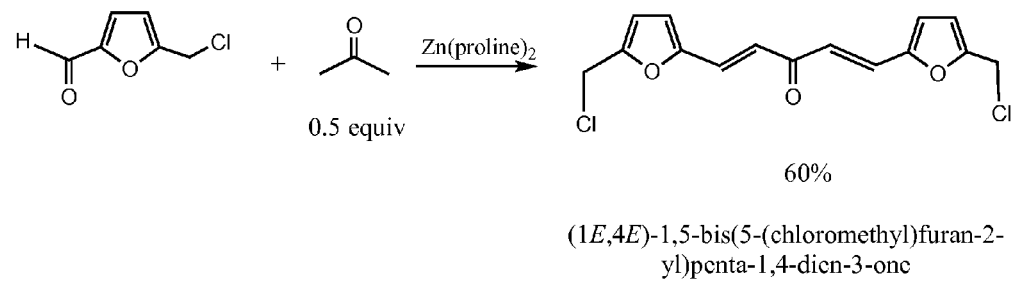
Figure 2:
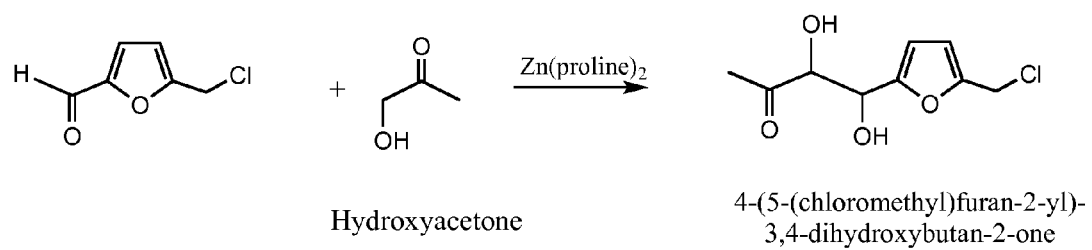
FIG. 2 depicts the reaction between chloromethylfurfural with hydroxyacetone to form the hydrocarbon product 4-(5-(chloromethyl)furan-2-yl)-3,4-dihydroxybutan-2-one.
Figure 3:
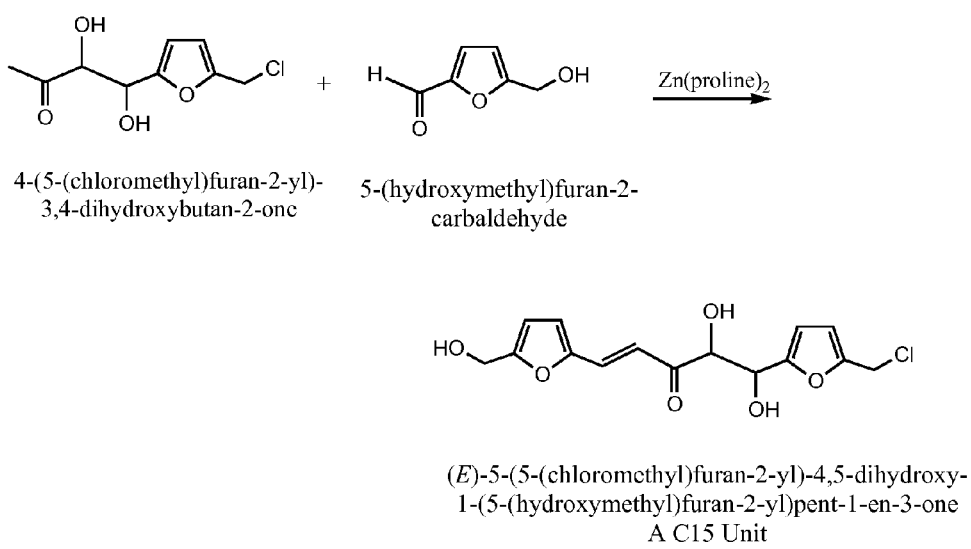
FIG. 3 depicts the reaction of 4-(5-(chloromethyl)furan-2-yl)-3,4-dihydroxybutan-2-one with 5-(hydroxymethyl)furan-2-carbaldehyde to form the $C_{15}$ hydrocarbon (E)-5-(5-(chloromethyl)furan-2-yl)-4,5-dihydroxy-1-(5-(hydroxymethyl)furan-2-yl)pent-1-en-3-one.
Figure 4:
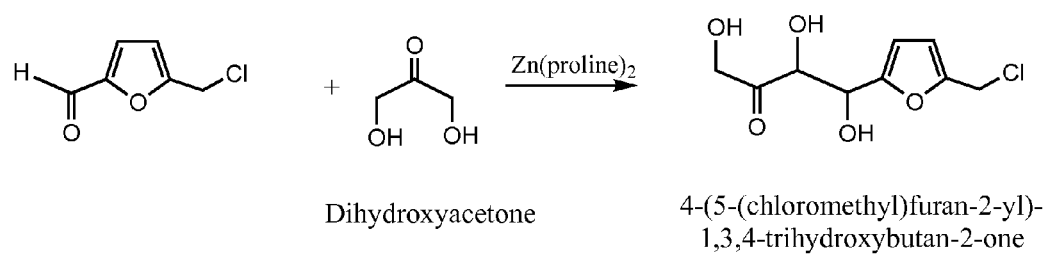
FIG. 4 depicts the reaction of dihydroxyacetone with chloromethylfurfural to form the hydrocarbon product 4-(5-(chloromethyl)furan-2-yl)-1,3,4-trihydroxybutan-2-one.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

The present invention relates to a method of producing $C_8$-$C_{15}$ hydrocarbons by increasing the carbon chain length of carbohydrates, which may be derived from herbaceous and woody biomass. As used herein, "hydrocarbons" is understood to include alcohols, olefins, ketones and other compounds comprising carbon, hydrogen and oxygen (as depicted in FIGS. 1-4), and is not intended to mean only compounds consisting of carbon and hydrogen atoms. Suitable reagents may be obtained from abundant chemical feedstocks such as glycerin. The method results in production of $C_8$-$C_{15}$ hydrocarbons, which may be subsequently hydrogenated and dehydrated to produce, among other compounds, transportation fuels and surfactants. The method utilizes the aldol reaction, also known as the aldol condensation reaction, which forms a carbon-carbon bond between an aldehyde and a ketone (herein referred to as an "aldehyde reagent" and a "ketone reagent," respectively).

Aldehyde reagents suitable for use in the present invention include, but are not limited to, chloromethylfurfural (CMF, CAS #1623-88-7) and furan-2-carbaldehyde. Other halide-substituted methylfurfurals also may be suitable, such as bromomethylfurfural and iodomethylfurfural. The carbon atom adjacent to the halide-substituted methyl group allows conversion to desirable alcohol and olefin end products. In addition, cellulose may also be converted directly to chloromethylfurfural, as described in Mascal et al., Angew. Chem. Int. Ed., 47, pp 7924-7926 (2008). Suitable ketone reagents in the present invention include acetone, dihydroxyacetone (DHA), methylacetoacetate, ethylacetoacetate, and combinations thereof.

The reaction of the aldehyde and ketone reagents proceeds in the presence of a suitable catalyst. A suitable catalyst must allow the reaction to proceed at room temperature, with water as a solvent, and result in a selectively high yield of the desired product. One suitable catalyst of the present invention is $Zn(Proline)_2$, which may have the following structure:

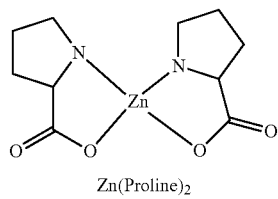

$Zn(Proline)_2$

Another suitable catalyst is $Yb(Proline)_3$, or $Yb(Pro)_3$, which has a structure similar to $Zn(Proline)_2$, wherein the Zn is replaced by Yb.

Other suitable catalysts include the following structures (I), (II) and (III):

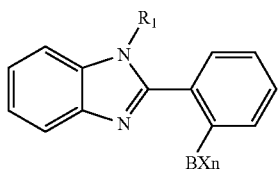

(I)

where $R_1$ is a $C_1$-$C_6$ alkyl moiety, where "alkyl" is understood to mean a substituted or unsubstituted alkane, alkene or alkyne, X=(OH) and n=2.

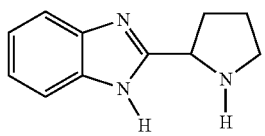

(II)

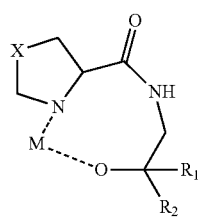

(III)

In (III), X may be $CH_2$, sulfur or selenium, M may be Zn, Mg, or a lanthanide, and $R_1$ and $R_2$ each independently may be a methyl, ethyl, phenyl moiety. It is to be understood that the phenyl group may comprise heteroatoms such as nitrogen or oxygen, provided that the atoms in $R_1$ or $R_2$ which are closest to the N-(2-hydroxy-2-methylpropyl)pyrrolidine-2-carboxamide core structure are a $CH_2$ group. In one embodiment, the reaction is performed in a solvent which comprises water and is substantially free of organic solvents. By "substantially free of organic solvents" is meant that the amount of organic solvent is about 1% or less. By "organic solvent" organic solvents other than water or salts that would be understood by one of skill in the art to be used in synthesis reactions, including but not limited to dimethylformamide (DMF), tetrahydrofuran (THF), alcohols, etc. The solvent further may comprise a salt, brine, saturated sodium chloride, or natural waters comprising salts. The reaction may be performed at room temperature (25° C.), and alternatively at a temperature of from about 0° C. to about 100° C. The reaction may have a yield of at least 60%, alternatively of at least 75%, alternatively of at least 90%, and alternatively of at least 99%. The reaction sequence can be tuned to give desired fuel properties by reaction with, for example, the DHA-furan complex, by employing selective regiochemistry.

EXAMPLES

Example 1

The reactions are performed in water without adjustment of pH. Piperidine was used in 5 mol %. Chloromethylfurfural (CMF) (0.631 g, 5.00 mmol) is charged in a small round bottom flask with a stirring bar, water (4.0 mL) is added. Acetone (0.290 g, 5.00 mmol (1 equivalent) or 0.25 mmol (0.5 equivalent) is then added (FIG. 1). The mixture is then stirred while piperidine was added at room temperature. The reaction mixture is kept closed with a plastic cap and stirred for 20 hrs. The stirring bar is removed and silica gel added. The mixture is dried with rotary evaporation. The residue is loaded on silica gel and eluted with 50% ethyl acetate in hexanes. Di-CMF adduct also is produced.

As would be understood by one of skill in the art, substitution of reagents as shown in FIGS. 1-4 under similar reaction conditions results in the products depicted in FIGS. 1-4.

Example 2

In a 100 mL single-necked round bottom flask was placed HOBT (hydroxybenzotriazole) (1.95 g), L-Boc-proline (3.00 g), and 2-hydroxy-2-methyl-propyl-1-amine. To this was added 70 mL of anhydrous acetonitrile. This was stirred until homogenous and then chilled to 0° C. The EDC (1-ethyl-3-(3-dimethylaminopropyl)carbodiimide), (3.20 g) was added in one portion to this mixture. The mixture was allowed to warm to room temperature and stirred overnight. The solvent was removed in vacuo. The remaining material was then taken up in 60 mL of methylene chloride and subsequently washed 4× with 10 mL of 5% citric acid. The suspension was filtered and dried over sodium sulfate. Filtration and removal of the solvent gave rise to the crude material. Purification by silica gel chromatography using 10% methanol/methylene chloride as eluent afforded 3.0336 g of an amide having the structure (IV), tert-butyl 2-(2-hydroxy-2-methylpropylcarbamoyl)pyrrolidine-1-carboxylate. $^1$H NMR (CDCl$_3$) d 4.29 (J=4.2 Hz, 1H), 3.45 (m, 2H), 3.26 (m 2H), 1.92 (m, 2H), 1.62 (m, 2H), 1.47 (s, 9H), 1.22 (s, 6H).

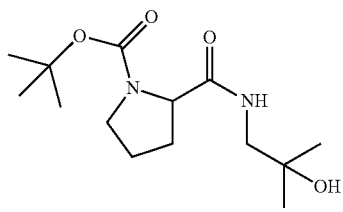 [SMILES: CC(C)(O)CNC(=O)C1CCCN1C(=O)OC(C)(C)C]

Whereas particular embodiments of the present invention have been illustrated and described, it would be clear to those skilled in the art that various other changes and modifications can be made without departing from the spirit and scope of the invention. It is therefore intended to cover in the appended claims all such changes and modifications that are within the scope of this invention.

What is claimed is:

1. A method of producing a $C_8$-$C_{15}$ hydrocarbon comprising:
    a) providing a ketone starting material;
    b) providing an aldol starting material comprising chloromethylfurfural; and
    c) mixing the ketone starting material and the aldol starting material in a reaction in the presence of a piperidinecontaining catalyst and a solvent, wherein the solvent comprises water that is substantially free of organic solvents, to produce the $C_8$-$C_{15}$ hydrocarbon.

2. The method of claim 1, wherein the ketone starting material comprises acetone, dihydroxyacetone, or combinations thereof.

3. The method of claim 1, wherein the reaction occurs at about 25° C.

4. The method of claim 1, wherein the solvent further comprises a salt.

5. The method of claim 1, further comprising hydrogenating and dehydrating the $C_8$-$C_{15}$ hydrocarbon.

* * * * *